United States Patent [19]

Briner

[11] Patent Number: 5,142,061

[45] Date of Patent: Aug. 25, 1992

[54] PROCESS FOR THE PREPARATION OF CYCLOPENTANE DERIVATIVES

[75] Inventor: Paul H. Briner, Canterbury, United Kingdom

[73] Assignee: Kureha Kagaku Kabushiki Kaisha, Tokyo, Japan

[21] Appl. No.: 591,154

[22] Filed: Oct. 1, 1990

Related U.S. Application Data

[63] Continuation-in-part of Ser. No. 399,885, Aug. 29, 1989, abandoned.

[30] Foreign Application Priority Data

Aug. 31, 1988 [GB] United Kingdom ............... 8820607

[51] Int. Cl.$^5$ ................. C07D 249/08; C07D 233/60
[52] U.S. Cl. ............... 548/267.8; 548/262.2; 548/267.2; 548/267.4; 548/101; 548/341
[58] Field of Search ........... 548/262.2, 267.8, 341, 548/101, 267.2, 267.4

[56] References Cited

U.S. PATENT DOCUMENTS 4,876,353 10/1989 Kraatz ............................ 548/262

FOREIGN PATENT DOCUMENTS

| | | |
|---|---|---|
| 0267778 | 5/1988 | European Pat. Off. |
| 0329397 | 2/1989 | European Pat. Off. |
| 0358259 | 3/1990 | European Pat. Off. |
| 0359305 | 3/1990 | European Pat. Off. |
| 0361560 | 4/1990 | European Pat. Off. |

*Primary Examiner*—Patricia L. Morris
*Attorney, Agent, or Firm*—Nixon & Vanderhye

[57] ABSTRACT

The present invention discloses a process to produce a compound of the formula (IA):

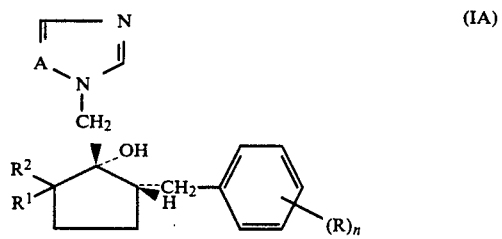

or an acid addition salt or metal complex thereof, in which n represents an integer from 0 to 5; each R represents a halogen atom, or a nitro, cyano, alkyl, haloalkyl or phenyl group; $R^1$ and $R^2$ independently represent a hydrogen atom or an alkyl group; and A represents a nitrogen atom or a CH group; which comprises steps of:
(1-a) reacting a compound of the formula (VI):

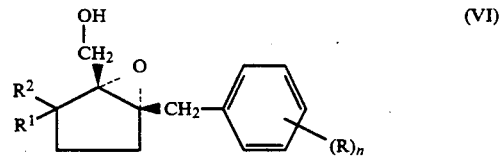

in which $n, R, R^1$ and $R^2$ are as defined above, with a reducing agent to obtain a compound of the formula (IVA); or, as an alternative step,
(1-b) reacting a compound of the formula (VII):

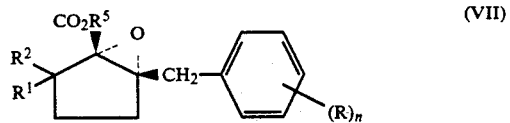

in which $n, R, R^1$ and $R^2$ are as defined above and $R^5$ represents a hydrogen atom or an alkyl group, with a reducing agent to obtain a compound of the formula (IVA);
(2) reacting a compound of the formula (IVA):

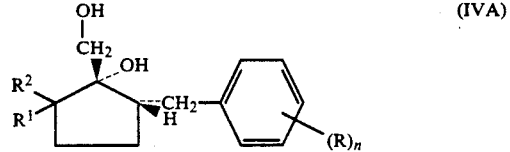

with a compound of the formula (V):

$$R^3SO_2X \quad (V)$$

in which $n, R, R^1$ and $R^2$ are as defined above and $R^3$ represents a $C_{1-4}$ alkyl group or a phenyl group each optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkyl, amino, $C_{1-4}$ alkylamino, di-$C_{1-4}$ alkylamino, $C_{1-4}$ alkoxycarbonyl, carboxyl, $C_{1-4}$ alkanoyl, $C_{1-4}$ alkylthio, $C_{1-4}$ alkylsulphinyl, $C_{1-4}$ alkylsulphonyl, carbamoyl, $C_{1-4}$ alkylamido, $C_{3-8}$ cycloalkyl and phenyl groups and X represents a halogen atom, in the presence of a base to obtain a compound of the formula (IIA);
(3) reacting a compound of the formula (IIA):

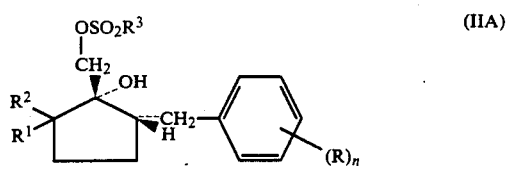

with a compound of the formula (III):

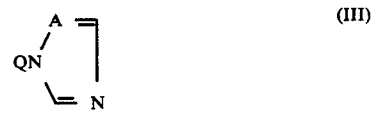

in which $n, R, R^1, R^2, R^3$ and A are as defined above and Q represents a hydrogen or alkali metal atom, in the presence of a base to obtain a compound of the formula (IA), and optionally converting the resulting compound of the formula (IA) into an acid addition salt or metal complex thereof.

2 Claims, No Drawings

PROCESS FOR THE PREPARATION OF CYCLOPENTANE DERIVATIVES

CROSS-REFERENCE TO RELATED APPLICATION

The present application is a continuation-in-part of application Ser. No. 399,885 filed Aug. 29, 1989, now abandoned.

BACKGROUND OF THE INVENTION

This invention relates to a process for the preparation of fungicidally active cyclopentane derivatives.

EP-A2-0267778 discloses fungicidally active cyclopentane derivatives of the formula:

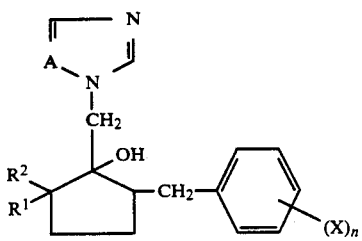

or acid addition salts or metal complexes thereof, in which $R^1$ and $R^2$ each independently represents a $C_{1-5}$ alkyl group or a hydrogen atom, each X represents a halogen atom, a $C_{1-5}$ alkyl group or a phenyl group, n represents 0, 1 or 2 and A represents a nitrogen atom or a CH group, provided that $R^1$ is not a hydrogen atom when $R^2$ is a hydrogen atom.

GB-A1-2180236 discloses fungicidally active cyclopentane derivatives of the above formula in which $R^1$ and $R^2$ both represent hydrogen atoms, n represents an integer from 1 to 5, each X represents a hydrogen atom, a halogen atom, an alkyl group, a haloalkyl group, a phenyl group, a cyano group or a nitro group and A represents a nitrogen atom or a CH group.

The compounds disclosed in EP-A2-0267778 and GB-A1-2180236 exist in two stereoisomeric forms which have the following structures:

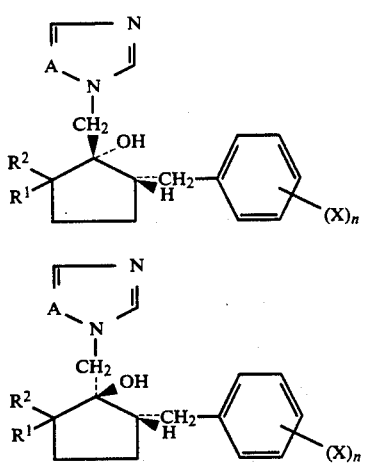

The letters A and B will be used hereinafter to denote compounds having the same stereochemical configuration as isomers A and B above.

Isomers A and B can be separated by, for instance, chromatography and exhibit different fungicidal activity. Generally, isomers of the formula A exhibit greater fungicidal activity than isomers of the formula B.

The processes for the preparation of the above compounds disclosed in GB-A1-2180236 and EP-A2-0267778 produce a mixture of isomers of the formulae A and B thereby necessitating the inclusion of an isomer separation step in the process. Moreover, production of the more active isomer A is not maximised in such processes because a portion of the starting materials is consumed in the simultaneous generation of the less active isomer B. However, a new process has now been discovered for the preparation of such compounds which is highly stereospecfic in favour of the more active isomer A.

SUMMARY OF THE INVENTION

An object of the present invention is to provide a process to prepare a compound of the formula:

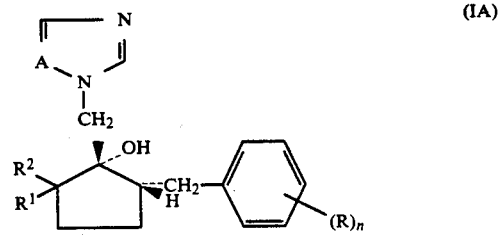

(IA)

or an acid addition salt of metal complex thereof, which comprises steps of:

(1-a) reacting a compound of the formula:

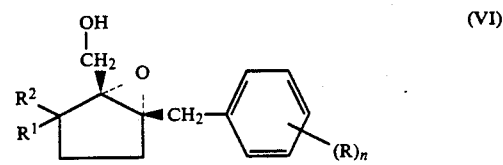

(VI)

or as an alternative step:

(1-b) reacting a compound of the formula:

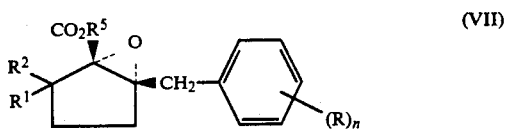

(VII)

with a reducing agent to obtain a compound of the formula (IVA):

(2) reacting a compound of the formula:

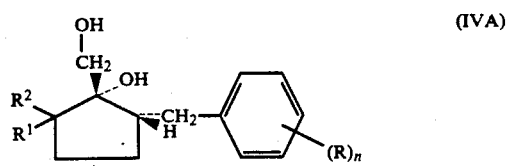

(IVA)

with a compound of the formula $$R^3SO_2X \quad (V)$$

in the presence of a base to obtain a compound of the formula (IIA):

(3) reacting a compound of the formula:

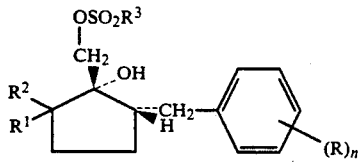

with a compound of the formula:

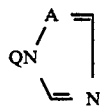

in the presence of a base to obtain a compound of the formula (IA), and optionally converting the resulting compound of the formula (IA) into an acid addition salt or metal complex thereof.

In the above formulae, n represent an integer from 0 to 5; each R represents a halogen atom or a nitro, cyano, alkyl, haloalkyl or phenyl group; $R^1$ and $R^2$ independently represent a hydrogen atom or an alkyl group; $R^3$ represents a $C_{1-4}$ alkyl group or a phenyl group, each optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, $C_{1-4}$ alkoxycarbonyl, carboxyl, $C_{1-4}$ alkanoyl, $C_{1-4}$ alkylthio, $C_{1-4}$ alkylsulphinyl, $C_{1-4}$ alkylsulphonyl, carbamoyl, $C_{1-4}$ alkylamido, $C_{3-8}$ cycloalkyl and phenyl groups; $R^5$ represents a hydrogen atom or an alkyl group; X represents a halogen atom; Q represents a hydrogen or alkali metal atom and A represents a nitrogen atom or a CH group.

DETAILED DESCRIPTION OF THE INVENTION

According to the present invention there is therefore provided a process for the preparation of a compound of the formula:

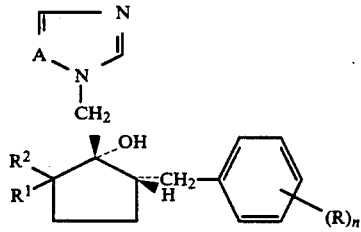

or an acid addition salt or metal complex thereof, in which n represents an integer from 0 to 5, each R represents a halogen atom, a nitro, cyano, alkyl, haloalkyl or phenyl group, $R^1$ and $R^2$ independently represent a hydrogen atom or an alkyl group, and A represents a nitrogen atom or a CH group; which comprises reacting a compound of the formula:

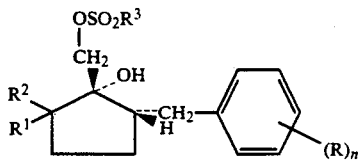

in which n, R, $R^1$ and $R^2$ are as defined above and $R^3$ represents a $C_{1-4}$ alkyl group or a phenyl group each optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, $C_{1-4}$ alkoxycarbonyl, carboxyl, $C_{1-4}$ alkanoyl, $C_{1-4}$ alkylthio, $C_{1-4}$ alkylsulphinyl, $C_{1-4}$ alkylsulphonyl, carbamoyl, $C_{1-4}$ alkylamido, $C_{3-8}$ cycloalkyl and phenyl groups, preferably a $C_{1-4}$ alkyl group or phenyl group each optionally substituted by one or more substituents selected from halogen atoms, nitro and $C_{1-4}$ alkyl groups; with a compound of the formula:

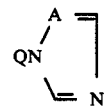

in which A is as defined above and Q represents a hydrogen or alkali metal, preferably sodium, atom, in the presence of a base; and, optionally, converting the resulting compound of the formula (I) into an acid addition salt or metal complex thereof.

It is preferred that the base is an inorganic base, such as potassium carbonate, potassium hydroxide, sodium carbonate and sodium hydroxide. Preferably, two equivalents of base are used.

The process may be carried out in the presence of a solvent, Suitable solvents include N-methylpyrrolidone, acetonitril, dimethylformamide, dimethylsulphoxide and high boiling ketones, such as methyl isobutyl ketone.

The reaction is carried out preferably at a temperature from 80° to 170° C., depending on the nature of the solvent, if present. The more preferable temperature is from 100° to 150° C.

When any of the substituents R, $R^1$ and $R^2$ represents or contains an alkyl substituent group, this may be linear or branched and may contain up to 12, preferably up to 6, and especially up to 4, carbon atoms. A cycloalkyl substituent group contain 3 to 8, preferably 3 to 6, carbon atoms.

It is preferred that $R^1$ and $R^2$ independently represent a hydrogen atom or a $C_{1-4}$ alkyl, particularly methyl, group.

Preferably, R represents a halogen, especially a chlorine, atom.

It is particularly preferred that n is 1, R represents a chlorine atom, preferably substituted at the 4-position of the phenyl ring, $R^1$ and $R^2$ both represent a hydrogen atom or both represent a methyl group and A represents a nitrogen atom.

Compounds of formula (IIA) can be prepared by reacting a compound of the formula:

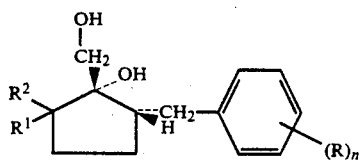

(IVA)

in which n R, $R^1$ and $R^2$ are as defined above, with a compound of the formula:

$$R^3SO_2X \qquad (V)$$

in which $R^3$ is as defined above and X represents a halogen, preferably chlorine or bromine, atom in the presence of a base.

It is preferred that the base is an organic base and, in particular, a tertiary base, which include triethylamine, tributylamine and pyridine.

The process may be carried out in the presence of a solvent. Preferable solvents include hydrocarbons, such as toluene, and chlorinated hydrocarbons, such as dichloromethane.

The reaction is suitably carried out at a low temperature, the preferred temperature being from −20° C. to room temperature. A particularly preferable temperature range is from −10° to 20° C.

The compounds of the formula (IIA) and a process for their preparation form the subject of U.S. patent application Ser. No. 397,720.

Compounds of the formula (IVA) can be prepared either by reacting a compound of the formula:

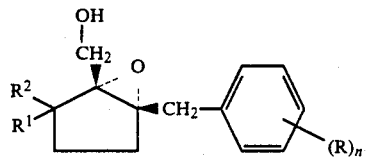

(VI)

in which n R, $R^1$ and $R^2$ are as defined above, with a suitable reducing agent, for instance, a complex metal hydride, such as lithium aluminum hydride, preferably at a temperature from 35° C. to reflux temperature; or by reacting a compound of the formula:

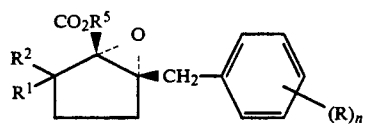

(VII)

in which n, R, $R^1$ and $R^2$ are as defined above and $R^5$ represents a hydrogen atom or an alkyl, preferably $C_{1-4}$ alkyl, group, with a reducing agent, such as lithium aluminium hydride, preferably at a temperature from 35° C. to reflux temperature.

The process can preferably be carried out in the presence of a solvent, for instance, lower ethers such as diethyl ether, tetrahydrofuran and high ethers, such as glymes, e.g., 1,2-dimethoxyethane.

It is preferable to destroy any excess reducing agent remaining at the end of the reduction process to prevent further reaction. If a complex metal hydride, such as lithium aluminium hydride, is used as a reducing agent, any excess may be destroyed by the addition of water and sodium hydroxide or ammonium chloride to the reaction mixture.

These reactions are stereospecific due to the presence of the epoxy group in the starting materials of the formula (VI) and the formula (VII). It has been found that the regioselectivity of these reactions may be improved further by the addition of a Lewis acid, such as aluminium chloride. The compounds of the formula (IVA) and a process for their preparation form the subject of U.S. patent application Ser. No. 397, 720.

Compounds of the formula (VI) can be prepared by reacting a compound of a formula (VII), as defined above, with a reducing agent, preferably a complex metal hydride, such as lithium aluminium hydride, sodium aluminium hydride, "REDAL" (Trade Mark: sodium bs(2-methoxyethoxy)aluminium hydride in toluene) or sodium borohydride, optionally in the presence of a Lewis acid, such as aluminium chloride. Epecially preferably reducing agent is lithium aluminium hydride, preferably at a temperature from room temperature to 85° C. The compounds of the formula (VI) and a process for their preparation form the subject of U.S. patent application Ser. No. 397,720.

Compounds of the formula (VII) can be prepared by reacting a compound of the formula:

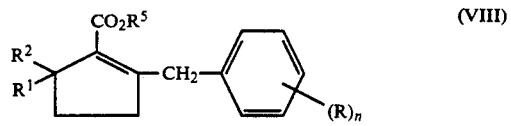

(VIII)

in which n, R, $R^1$ and $R^5$ are as defined above, with a peracid. Preferably 1 to 3 equivalents of peracid may be used. Preferably peracid is peractic acid perbenzoic acid or periphathalic acid. In the case of peracetic acid, this may be generated in situ, if desired, by reacting hydrogen peroxide with acetic acid.

The process ma be carried out in the presence of a solvent. Suitable solvents include chlorinated solvent, such as dischloromethane and trichloromethane, esters and aromatic hydrocarbons.

The reaction can be carried out preferably at a temperature from room temperature to the reflux temperature of the solvent, if used. The especially preferable temperature is from 30° to 70° C.

The compounds of the Formula (VII) and a process for their preparation from the subject of U.S. patent application Ser. No. 397,288.

Compounds of the formula (VIII) can be prepared by heating a compound of the formula:

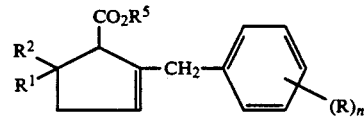

(IX)

or of the formula:

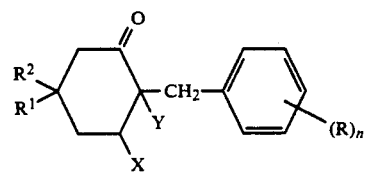

(X)

in which n, R, $R^2$, $R^2$ and $R^5$ are as defined above and X and Y independently represent a halogen, preferably chlorine or bromine, atom, with a compound of the formula:

MOR$^5$ (XI)

in which $R^5$ is as defined above and M represents an alkali metal, preferably sodium, atom, in the presence of a polar solvent. It is preferred that the polar solvent is compound of the formula:

R$^5$OH (XII)

in which $R^5$ is as defined above. Preferably, $R^5$ has the same meaning in the formula (XI) and the formula (XII). For instance, if the compound of the formula (XI) is sodium methoxide, it is preferred that the solvent of the formula (XII) is methanol. The reaction is preferably carried out at a temperature from 0° C. to reflux temperature. Preferably, an excess of the compound (XII) is used. The compounds of the formula (VIII) and a process for their preparation form the subject of U.S. patent application Ser. No. 397,756.

Compounds of the formula (IX) can be prepared by reacting a compound of the formula (X), as defined above, with a compound of the formula (XI), as defined above, in the presence of a polar solvent, preferably a solvent (XII), as defined above preferably at a temperature from 0° C. to the reflux temperature of the solvent, more preferably in the range of 0° to 20° C. The compounds of the formula (IX) and a process for their preparation form the subject of U.S. patent application Ser. No. 397,756.

Compounds of the formula (X) can be prepared by reacting a compound of the formula:

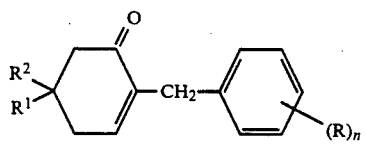 (XIII)

in which n, R, $R^1$ and $R^2$ are as defined above, with a compound XY, in which X and Y are as defined above. Alternatively, compounds of the formula (X) may be generated in situ and then heated with a compound of the formula (XI) in the presence of a solvent of the formula (XII) as described above to form compounds of the formula (VIII) in a one-pot synthesis.

The process can preferably be carried out in the presence of a solvent. Preferable solvent include petroleum, lower alcohols, chlorinated hydrocarbons, ethers and acetic acid. The reaction can be carried out preferably at a temperature from −10° C. to room temperature, more preferably from 0° C. to room temperature, Compounds of the formula (X) and a process for their preparation form the subject of U.S. patent application Ser. No. 397,756.

Compounds of the formula (XIII) can be prepared by reacting a compound of the formula:

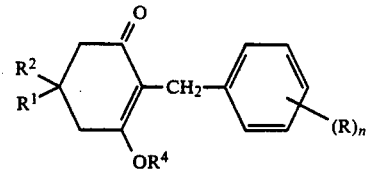 (XIV)

in which n, R, $R^1$ and $R^2$ are as defined above and $R^4$ represents an alkyl, preferably $C_{1-4}$ alkyl, group, with a suitable reducing agent, for instance, a complex metal hydride, such as lithium aluminium hydride, sodium aluminium hydride, and "REDAL" [Trade Mark: sodium bis(2-methoxyethoxy)aluminium hydride in toluene], or hydrogen in combination with a catalyst.

The process is preferably carried out in the presence of a solvent and preferable solvents include ethers, such as diethyl ether, tetrahydrofuran and oligoethers, and hydrocarbons. The reaction can be carried out preferably at a temperature from 20° to 80° C.

It is preferable to destroy any excess reducing agent remaining at the end of the reduction process to prevent further reaction. If a complex metal hydride, for instance, lithium aluminium hydride is used as reducing agent, any excess may be destroyed by the addition of water and sodium hydroxide to the reaction mixture.

This process for preparing compounds of the formula (XIII) proceeds via an enol ether intermediate. Accordingly, to obtain compounds of the formula (XIII), it is necessary to include a hydrolysis work-up in the above process. This may comprise the addition of a dilute mineral acid, such as hydrochloric acid to the reaction mixture after the reduction step and serves to convert any remaining intermediate enol ether into the desired cyclohexenone derivatives of the formula (XIII).

The compounds of the formula (XIII) and a process for their preparation form the subject of U.S. patent application Ser. No. 397,756.

Compounds of the formula (XIV) can be prepared by reacting a compound of the formula:

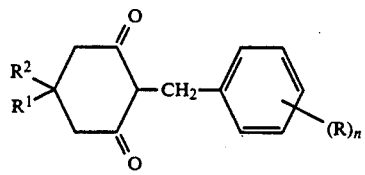 (XV)

in which n, R, $R^1$ and $R^2$ are as defined above, with a compound of the formula:

R$^4$OH (XVI)

in which $R^4$ is as defined above, in the presence of an acid, and if desired, the compound of the formula (XIV) so obtained can be converted into another compound of the formula (XIV) by reaction with a second different compound of the formula (XVI) in the presence of an acid.

The acid may be any substance which acts as a source of proton. Suitable acids include inorganic acid such as sulphuric acid, organic acid such as p-toluenesulphonic acid and an ion exchange resin.

The process can preferably be carried out in the presence of a solvent. Suitable solvents include petroleum, toluene and benzene. Solvents which form azeotropic mixtures with the reactants are particularly preferred.

The reaction can suitably carried out preferably at a temperature from 70° to 130° C. and more preferably from 80° to 120° C.

The compounds of the formula (XIV) and a process for their preparation form the subject of U.S. patent application Ser. No. 397,756.

Compounds of the formula (XV) can be prepared by reacting a compound of the formula:

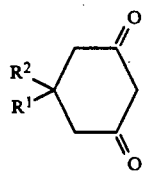

in which R¹ and R² are as defined above, with a compound of the formula: in which R and n are as defined above and L represents a suitable leaving group, in the presence of a suitable base, such as potassium hydroxide. The compounds of the formula (XV) form the subject of U.S. patent application Ser. No. 397,756.

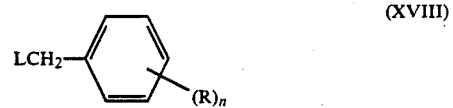

Compounds of the formulae (III), (V), (XI), (XII), (XVI), (XVII) and (XVIII) and the compounds XY are known compounds or can be prepared by processes analogous to known processes.

The overall process used to synthesise compounds of the formula (IA) starting from compounds of the formula (XVII) and the formula (XVIII), as described above, is set out in the following reaction scheme:

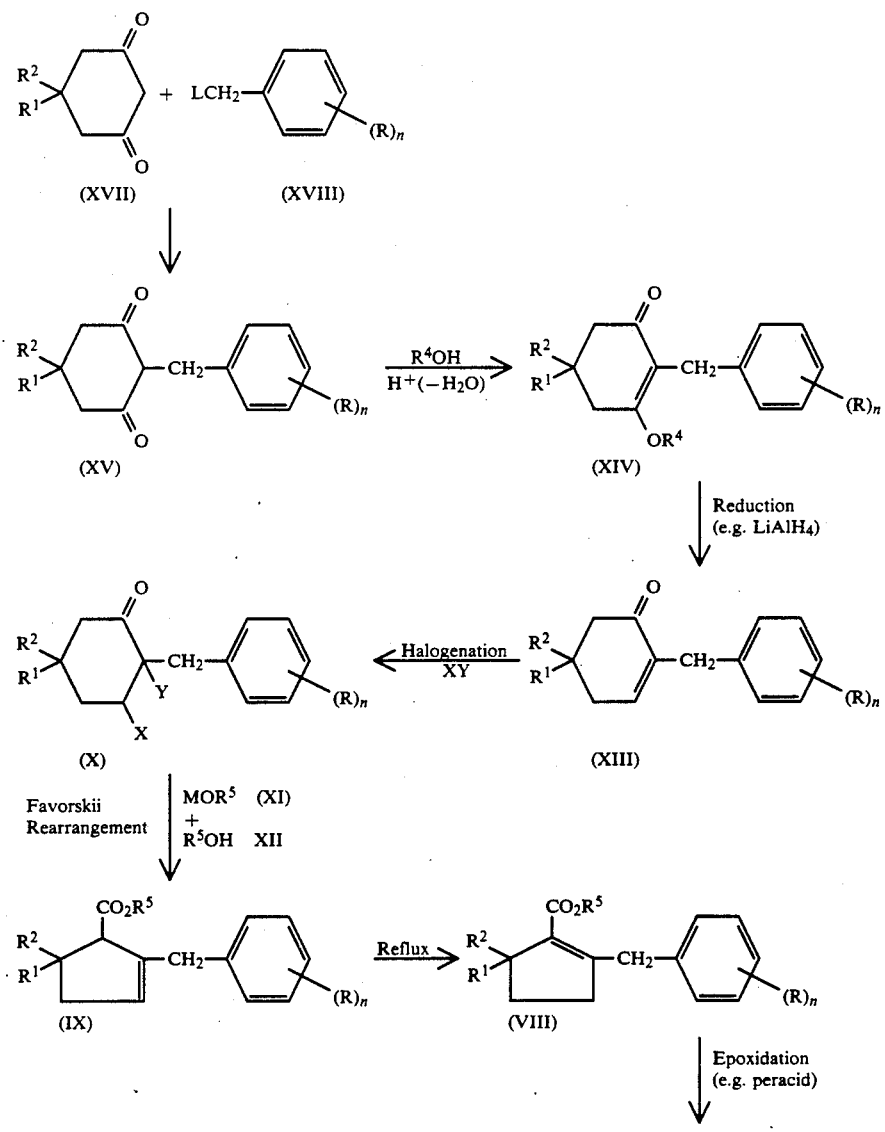

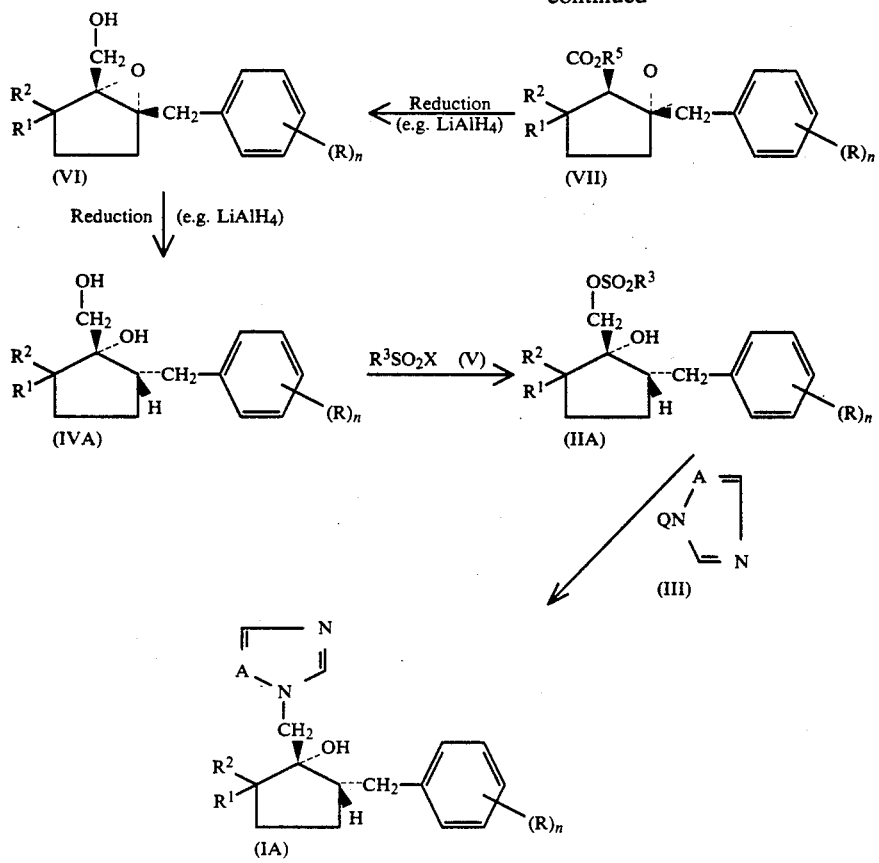

In the above reaction scheme, n, R, $R^1$, $R^2$, $R^3$, $R^4$, $R^5$, X, Y, L, M, Q and A are as previously defined.

The invention is further illustrated by the following Examples.

EXAMPLE 1

Preparation of 1-)4-chlorobenzyl)-3,3-dimethyl-2-hydroxy-2-(1,2,4-triazol-1-yl)methylcyclopentane (Isomer A)

(n=1, R=4-Cl, $R^1=R^2=CH_3$, A=N)

(a) Preparation of 2-(4-chlorobenzyl)-5,5-dimethylcyclohexane-1,3-dione 449 g (3.21 mols) dimedone (5,5-dimethylcyclohexane-1,3-dione) were added to a solution of aqueous potassium hydroxide comprising 166 g of 85% potassium hydroxide (2.52 mols) in 700 ml of water. The mixture was then warmed and a clear orange solution was obtained at 47° C. The solution was then heated to 59° C. and 544 g (3.21 mols) molten 4-chlorobenzyl chloride were added over a period of 1 hour with further heating to 85° C. Heating was continued for a further 2.5 to 3 hours up to a temperature of 100° C. The mixture was then cooled, the solid product filtered off, washed with water and dried in a vacuum oven at 50° C. The crude solid (815 g) was then dissolved in 2,400 ml methanol at reflux and 200 ml water added to produce a permanent cloudiness. The mixture was then allowed to cool to room temperature overnight with stirring. The solid so obtained was filtered, washed with about 400 ml cold methanol and dried in a vacuum oven to produce 340 g 2-(4-chlorobenzyl)-5,5-dimethylcyclohexane-1,3-dione as a white solid, m.pt. 188°–190° C. Yield: 42%.

(b) Preparation of 2-(4-chlorobenzyl)-3-(2-methylpropoxy)-5,5-dimethylcyclohex-2-en-1-one 325 g (1.23 mols) of 2-(4-chlorobenzyl)-5,5-dimethylcyclohexane-1,3-dione obtained in (a), 1.6 liters toluene, 182 g (2.5 mols) isobutanol and 5 g p-toluenesulphonic acid were stirred together at reflux under a Dean-Stark apparatus. The temperature of the reaction mixture was approximately 90° C. As water distilled off, the reaction mixture changed from a thin slurry to a yellow solution. After 14 hours reflux, the reaction mixture was cooled and shaken twice with 500 ml aliquots of 10% aqueous solution of sodium hydroxide. The toluene layer was then flashed to give 389 g yellow/orange oil which crystallised on standing. Recrystallisation of the solid from 60/80 petroleum produced 331 g 2-(4-chlorobenzyl)-3-(2-methylpropoxy)-5,5-dimethylcyclohex-2-en-1-one as a white crystalline solid, m.pt. 60°–61° C. Yield: 84%.

(c) Preparation of 2-(4-chlorobenzyl)-3-methoxy-5,5-dimethylcyclohex-2-en-1-one

A solution of 154 g of 2-(4-chlorobenzyl)-3-(2-methylpropoxy)-5,5-dimethylcyclohex-2-en-1-one obtained in (b) in 1,200 ml methanol containing 3 g p-toluenesulphonic acid was refluxed for 2 hours. The reaction mixture was then extracted with 3 liters water and 1 liter diethyl ether and re-extracted with a further 1 liter diethyl ether. The organic phases were then backwashed first with 200 ml 10% aqueous solution of sodium hydroxide and then with 100 ml saturated aqueous sodium chloride solution, dried over anhydrous magnesium sulphate and flashed. The residue was then crystallised in 60/80 petroleum, filtered and air-dried to give 98 g 2-(4-chlorobenzyl)-3-methoxy-5,5-dimethylcyclohex-2-en-1-one as a white solid, m.pt. 62°-63° C. Yield: 73%.

(d) Preparation of 2-(4-chlorobenzyl)-5,5-dimethylcyclohex-2-en-1-one 98 g (0.35 mol) of 2-(4-chlorobenzyl)-3-methoxy-5,5-dimethylcyclohex-2-en-1-one obtained in (c) were added to a slurry of 6.65 g (0.175 mol) lithium aluminium hydride in 490 ml diethyl ether at a rate sufficient to maintain reflux and the final reaction mixture refluxed for a further 30 minutes. 5 ml water were then added, followed by 5 ml 15% aqueous sodium hydroxide solution and a further 15 ml water and the resulting precipitate was filtered off. The filtrate was then shaken in 200 ml 5M hydrochloric acid for 5 minutes and the organic layer then separated, washed twice with 100 ml aliquots of saturated aqueous sodium bicarbonate solution, dried over anhydrous magnesium sulphate and stripped. The resulting oil was then dissolved in 430 ml dichloromethane, 18 g (0.085 mol) pyridinium chlorochromate was added and the reaction mixture stirred for 3 hours. 600 ml diethyl ether were added and the solid was then filtered off. The filtrate was washed three times with 10% aqueous solution of sodium hydroxide, once with 2.5M hydrochloric acid and once with saturated aqueous sodium bicarbonate solution. It was then dried over anhydrous magnesium sulphate and stripped to give 82 g of crude product. Distillation of the crude product under reduced pressure (0.15 mm mercury) give 79 g 2-(4-chlorobenzyl)-5,5-dimethylcyclohex-2-en-1-one, b.pt. 130° C. at 0.15 mm mercury. Yield: 91%.

(e) Preparation of 2-(4-chlorobenzyl)-(2,3-dibromo-5,5-dimethylcyclohexan-1-one 10 g (40.2 mmols) of 2-(4-chlorobernzyl)-5,5-dimethylcyclohex-2-en-1-one obtained in (d) were dissolved in 50 ml 30/40 petroleum at 0° C. 6.72 g (40.2 mmols) bromine were then added to the solution. After 5-10 minutes, the solution decolourised and a precipitate formed. The solution was then cooled further and the precipitate filtered off to give 12.4 g 2-(4-chlorobenzyl)-2,3-dibromo-5,5-dimethyl-cyclohexan-1-one as a solid, m.pt. 82°-84° C. Yield: 75%.

(f) Preparation of 1-(4-chlorobenzyl)-3,3-dimethyl-2-methoxycarbonylcyclopent-1-ene A solution of sodium methoxide was prepared by adding 2.8 g (121 mmols) sodium to 50 ml methanol. A slurry of 2-(4-chlorobenzyl-2,3-dibromo-5,5-dimethylcyclohexan-1-one obtained in (e) in methanol was then prepared and added to the sodium methoxide solution at reflux. Reflux was continued overnight. The reaction mixture was then quenched with 200 ml water, extracted twice with 100 ml aliquots of diethyl ether, backwashed with water, dried over anhydrous magnesium sulphate and flashed to give 8 g of a yellow oil. By gas chromatography analysis, it was established that 6.6 g 1-(4-chlorobenzyl)-3,3-dimethyl-2-methoxycarbonylcyclopent-1-ene was produced as an oil. The structure of the product was established by n.m.r. spectroscopy. Yield: 78%.

(g) Preparation of 1-(4-chlorobenzyl)-1,2-epoxy-3,3-dimethyl-2-methoxycarbonylcyclopentane 23.5 g (3 equivalents) "PROXITANE 4002" (Trade Mark: 36-40% (w/w) peracetic acid in acetic acid) were added to 9,8 g (35.1 mmols) 1-(4-chlorobenzyl)-3,3-dimethyl-2-methoxycarbonylcyclopent-1-ene prepared as described in (f) in 90 ml trichloromethane. The resulting mixture was refluxed for 3 hours and then extracted twice with 50 ml aliquots of trichloromethane, backwashed once with 50 ml dilute aqueous solution of sodium bicarbonate and twice with 50 ml aliquots of saturated aqueous solution of sodium metabisulphite, washed with saturated aqueous sodium chloride solution, dried over anhydrous magnesium sulphate and flashed to give 12 g of a pale yellow oil which crystallized on cooling. Trituration in 30/40 petroleum gave 5.8 g 1-(4-chlorobenzyl)-1,2-epoxy-3,3-dimethyl-2-methoxycarbonylcyclopentane as a white crystalline solid, m.pt. 86°-87° C. Yield: 56%.

(h) Preparation of 1(4-chlorobenzyl)-1,2-epoxy-3,3-dimethyl-2-hydroxymethylcyclopentane 10.7 g (36.3 mmols) 1-(4-chlorobenzyl)-1,2-epoxy-3,3-dimethyl-2-methoxycarbonylcyclopentane prepared as described in (g) were dissolved in diethyl ether and the resulting solution was then added to a slurry of 1.5 g (36.6 mmols) lithium aluminium hydride in 50 ml diethyl ether at a rate such that reflux of the reaction mixture was maintained. Heating was continued for 5 minutes after the last addition of 1-(4-chlorobenzyl)-1,2-epoxy-3,3-dimethyl-2 -methoxycarbonylcyclopentane solution. 1.25 ml water were then added, followed by 1.25 ml 15% aqueous sodium hydroxide solution and a further 4 ml water. The solid was filtered off and the filtrate was then dried over anhydrous magnesium sulphate and flashed to give a clear oil which crystallised on cooling to give 9.6 g 1-(4-chlorobenzyl)-1,2-epoxy-3,3-dimethyl-2-hydroxymethylcyclopentane as a solid. m.pt. 36°-38° C., which can be reduced to 1-(4-chlorobenzyl)-3,3-dimethyl-2-hydroxy-2-hydroxymethylcyclopentane in a conventional method.

(i) Preparation of 1-(4-chlorobenzyl)-3,3-dimethyl-2-hydroxy-2-hydroxymethylcyclopentane (Isomer A)

2.7 g (71 mmols) lithium aluminium hydride were added to a suspension of 2.7 g (24 mmols) aluminium chloride partially dissolved in 120 ml 1,2-dimethoxyethane, the addition of lithium aluminium hydride causing a rise in temperature to 50° C. The resulting slurry was incubated at 50° C. for 30 minutes. A solution of 6.8 g (23 mmols) 1-(4-chlorobenzyl)-1,2-epoxy-3,3-dimethyl-2-methoxycarbonylcyclopentane prepared as described in (g) in 30 ml 1,2-dimethoxyethane was then added over a period of 30 minutes whilst maintaining the temperature of the reaction mixture at 50°-55° C. After 1 hour, thin layer chromatography indicated that the reaction was complete and the excess lithium aluminium hydride was therefore destroyed by adding 10 ml saturated aqueous ammonium chloride solution followed by 10 ml water. This produced a sludgy solid which filtered only slowly. After filtration, the solid was dissolved in 2N hydrochloric acid and extracted twice with diethyl ether. The extracts were combined with the filtrate and flashed to give 5.9 crude product. Trituration with cold 60/80 petroleum and a little diethyl ether gave 5.45 g 1-(4-chlorobenzyl)-3,3-dimethyl-2-hydroxy-2-hydroxymethylcyclopentane as a white solid, m.pt. 103°–104° C. Yield: 82%.

(j) Preparation of 1-(4-chlorobenzyl)-3,3-dimethyl-2-hydroxy-2-methylsulphonyloxymethylcyclopentane (Isomer A)

2.76 g (1.05 equivalents)methylsulphonyl chloride were added to a solution of 6.42 g (24 mmols) 1-(4-chlorobenzyl)-3,3-dimethyl-2-hydroxy-2-hydroxymethylcyclopentane prepared as described in (i) and 2.55 g (1.1 equivalents) triethylamine in 50 ml dichloromethane at 10°–15° C. The reaction mixture was kept at 10°–15° C. for further 2 hours and then washed with 20 ml water, then 20 ml aqueous sodium bicarbonate solution, dried over anhydrous magnesium sulphate and flashed. Trituration with 60/80 petroleum gave 6.64 g 1-(4-chlorobenzyl)-3,3-dimethyl-2-hydroxy-2-methylsulphonyloxymethylcyclopentane (Isomer A) as a white solid, m.pt. 113°–114° C. Yield: 80%.

(k) Preparation of 1-(4-chlorobenzyl)-3,3-dimethyl-2-hydroxy-2-(1,2,4-triazol-1-yl)methylcyclopentane (Isomer A)

A mixture of 0.22 g (1-(4-chlorobenzyl)-3,3-dimethyl-2-hydroxy-2-methylsulphonyloxymethylcyclopentate prepared as described in (j), 47 mg 1,2,4-triaazole and 0.1 g potassium carbonate in 3 ml N-methylpyrrolidone was warmed at 50° C. for 2 hours. A further 0.1 g potassium carbonate was then added, the temperature was raised to 120° C. and the reaction continued overnight at this temperature. The reaction mixture was then partitioned between diethyl ether and water and the organic solution flashed to give (1-(4-chlorobenzyl)-3,3-dimethyl-2-hydroxy-2-(1,2,4-triazol-1-yl)methylcyclopentane crystallised from petroleum as a single stereoisomer (Isomer A). The conversion yield of Isomer A, corrected for purity, was 72%. The structure of the product was established by n.m.r. spectroscopy. Purity of Isomer A was 90% and Isomer B was not detected.

EXAMPLE 2

Preparation of 1-(4-chlorobenzyl)-3,3-dimethyl-2-hydroxy-2-(1,2,4-triazol-1-yl)methylcyclopentane (Isomer A)

(n=1,R=4-Cl,R$^1$=R$^2$=CH$_3$, A=N)

(a) Preparation of 2-(4-chlorobenzyl)-2,3-dibromo-5,5-dimethylcyclohexane-1-one 5 g of 2(4-chlorobenzyl)-5,5-dimethylcyclohex-2-en-1-one obtained in Example 1 (d) were dissolved in 25 ml tetrachloromethane at 5°–10° C. 3.2 g bromine were then added to the solution over a period of 10 minutes. The solution decolourised and 2-(4-chlorobenzyl)-2,3-dibromo-5,5-dimethylcyclohexan-1-one was formed in the solution.

(b) Preparation of 2-(4-chlorobenzyl)-4,4-dimethyl-3-methoxycarbonylcyclopent-1-ene A solution of sodium methoxide was prepared by adding 1.1 g sodium to 10 ml methanol. 50 ml methanol was then added to the reaction mixture obtained in (a) followed by the solution of sodium methoxide, keeping the temperature of the reaction mixture at 10°–15° C. After 2 hours, the mixture was partitioned between dichloromethane and water, backwashed with water, dried over anhydrous magnesium sulphate and flashed to give 5.65 g crude (2-(4-chlorobenzyl)-4,4-dimethyl-3-methoxycarbonylcyclopent-1-ene as an oil. The structure of the product was established by n.m.r. spectroscopy.

(c) Preparation of 1-(4-chlorobenzyl)-3,3-dimethyl-2-methoxycarbonylcyclopent-1-ene The crude 2(4-chlorobenzyl)-4,4-dimethyl-3-methoxycarbonylcyclopent-1-ene obtained in (b) was refluxed for 15 hours in methanol as solvent containing one equivalent of sodium methoxide to give 1-(4-chlorobenzyl)-3,3-dimethyl-2-methoxycarbonyl-cyclopent-1-ene as an oil.

(d) Preparation of 1(4-chlorobenzyl)-1,2-epoxy-3,3-dimethyl-2methoxycarbonylcyclopentane 23.5 g (3 equivalents) "PROXITANE 4002" (Trade Mark: 36–40% (w/w) peracetic acid in acetic acid) were added to 9.8 g (35.1 mmols) 1-(4-chlorobenzyl)-3,3-dimethyl-2-methoxycarbonylcyclopent-1-ene prepared as described in Example 1 (f) in 90 ml trichloromethane. The resulting mixture was refluxed for 3 hours and then extracted twice with 50 ml aliquots of trichloromethane, backwashed once with 50 ml dilute aqueous sodium bicarbonate solution and twice with 50 ml aliquots of saturated aqueous sodium metabisulphite solution, washed with saturated aqueous sodium chloride solution, dried over anhydrous magnesium sulphate and flashed to give 12 g of a pale yellow oil which crystallised on cooling. Trituration in 30/40 petroleum gave 5.8 g 1-(4-chlorobenzyl)-1,2-epoxy-3,3-dimethyl-2-methoxy-carbonylcyclopentane as a white crystalline solid, m.pt. 86°–87° C. Yield 56%.

(e) Preparation of 1-(4-chlorobenzyl)-3,3-dimethyl-2-hydroxy-2hydroxymethylcyclopentane (Isomer A)

2.7 g (71 mmols) lithium aluminium hydride were added to a suspension of 2.7 g (24 mmols) aluminium chloride partially dissolved in 120 ml 1,2-dimethyoxyethyane, the addition of lithium aluminium hydride causing a rise in temperature to 50° C. The resulting slurry was incubated at 50° C. for 30 minutes. A solution of 6.8 g (23 mmols) 1-(4-chlorobenzyl)-1,2-epoxy-3,3-dimethyl-2-methoxycarbonylcyclopentane prepared as described in Example 1 (g)in 30 ml 1,2-dimethoxyethane was added over a period of 30 minutes whilst maintaining the temperature of the reaction mixture at 50°–55° C. After 1 hour, thin layer chromatography indicated that the reaction was complete and the excess lithium aluminium hydride was therefore destroyed by adding 10 ml saturated aqueous ammonium chloride solution followed by 10 ml water. This produced a sludgy solid which was filtered only slowly. After filtration, the solid was dissolved in 2N hydrochloric acid and extracted twice with diethyl ether. The extracts were combined with the filtrate and flashed to give 5.9 g crude product. Trituration with cold 60/80 petroleum and a little diethyl ether gave 5.45 g 1-(4-chlorobenzyl)-3,3-dimethyl-2-hydroxy-2-hydroxy-methylcyclopentane as a white solid, m.pt. 103°–104° C. Yield: 82%.

(f) Preparation of 1-(4-chlorobenzyl)-3,3-dimethyl-2-hydroxy-2-methyl-sulphonyloxymethylcyclopentane (Isomer A)

2.76 g (1.05 equivalents) methylsulphonyl chloride were added to a solution of 6.42 g (24 mmols) 1-(4-chlorobenzyl)-3,3-dimethyl-2-hydroxy-2-hydroxymethylcyclopentane prepared as described in Example 1 (i) and 2.55 g (1.1 equivalents) triethylamine in 50 ml dichloromethane at 10°–15° C. The reaction mixture was kept at 10°–15° C. for further 2 hours and then washed with 20 ml water, then 20 ml aqueous sodium bicarbonate solution, dried over anhydrous magnesium sulphate and flashed. Trituration with 60/80 petroleum gave 6.64 g 1-(4-chlorobenzyl)-3,3-dimethyl-2-hydroxy-2-methyl-sulphonyloxymethylcyclopentane (Isomer A) as a white solid, m.pt. 113°–114° C. Yield: 80%.

(g) Preparation of 1-(4-chlorobenzyl)-3,3-dimethyl-2-hydroxy-2-(1,2,4-triazol-1-yl)methylcyclopentane (Isomer A)

A mixture of 0.22 g 1-(4-chlorobenzyl)-3,3-dimethyl-2-hydroxy-2-methylsulphonyloxymethylcyclopenane prepared by described in Example 1 (j), 47 mg 1,2,4-triazole and 0.1 g potassium carbonate in 3 ml N-methylpyrrolidone was warmed at 50° C. for 2 hours. A further 0.1 g potassium carbonate was then added, the temperature was raised to 120° C. and the reaction continued overnight at this temperature. The reaction mixture was then partitioned between diethyl ether and water and the organic solution flashed to give (1-(4-chlorobenzyl)-3,3-dimethyl-2-hydroxy-2-(1,2,4-triazol-1-yl)methylcyclopentane crystallised from petroleum as a single stereoisomer (Isomer A). The conversion yield of Isomer A, corrected for purity, was 72%. The structure of the product was established by n.m.r. spectroscopy. Purity of Isomer A was 90% and Isomer B was not detected.

What is claimed is:

1. A process for the preparation of a compound of the formula (IA):

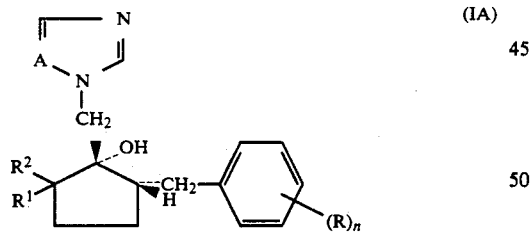

or an acid addition salt or metal complex thereof, in which n represents an integer from 0 to 5; each R represents a halogen atom, or a nitro, cyano, alkyl, haloalkyl or phenyl group; $R^1$ and $R^2$ independently represent a hydrogen atom or an alkyl group; and A represents a nitrogen atom or a CH group; which comprises steps of:

(1-a) reacting a compound of the formula (VI):

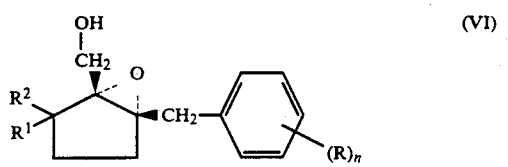

in which $n, R, R^1$ and $R^2$ are as defined above, with a boron hydride or aluminium hydride derivative reducing agent to obtain a compound of the formula (IVA); or, as an alternative step, (1-b) reacting a compound of the formula (VII):

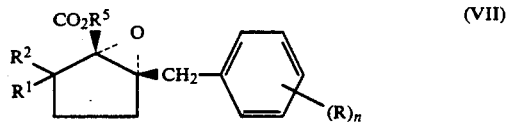

in which, $n, R, R^1$ and $R^2$ are as defined above and $R^5$ represents a hydrogen atom or an alkyl group, with said reducing agent to obtain a compound of the formula (IVA);

(2) reacting a compound of the formula (IVA):

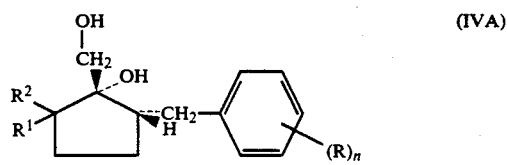

with a compound of the formula (V):

in which $n, R, R^1$ and $R^2$ are as defined above and $R^3$ represents a $C_{1-4}$ alkyl group or a phenyl group each optionally substituted by one or more substitutents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, $C_{1-4}$ alkoxycarbonyl, carboxyl, $C_{1-4}$ alkanoyl, $C_{1-4}$ alkylthio, $C_{1-4}$ alkylsulphinyl, $C_{1-4}$ alkylsulphonyl, carbamoyl, $C_{1-4}$ alkylamido, $C_{3-8}$ cycloalkyl and phenyl groups and X represents a halogen atom, in the presence of a base to obtain a compound of the formula (IIA);

(3) reacting a compound of the formula (IIA):

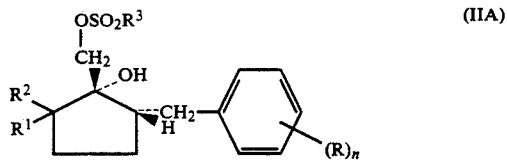

with a compound of the formula (III):

in which $n, R, R^1, R^2, R^3$ and A are as defined above and Q represents a hydrogen or alkali metal atom, in the presence of a base to obtain a compound of the formula (IA), and optionally converting the resulting compound of the formula (IA) into an acid addition salt or metal complex thereof.

2. The process according to claim 1, wherein a purity of said compound of the formula (IA) is not lower than 90%.

* * * * *